United States Patent [19]

Ensslin

[11] Patent Number: 4,938,761
[45] Date of Patent: Jul. 3, 1990

[54] BIPOLAR ELECTROSURGICAL FORCEPS

[75] Inventor: Frieder H. Ensslin, Rochester, N.Y.

[73] Assignee: MDT Corporation, Torrance, Calif.

[21] Appl. No.: 319,050

[22] Filed: Mar. 6, 1990

[51] Int. Cl.⁵ ............................................. A61B 17/39
[52] U.S. Cl. ........................................ 606/51; 606/40;
606/52
[58] Field of Search .................. 128/303.13, 303.14,
128/303.17, 303.18; 219/230, 241; 606/43, 48,
51, 52, 36–40

[56] References Cited

U.S. PATENT DOCUMENTS

| | | |
|---|---|---|
| 3,685,518 | 8/1972 | Beuerle et al. .................. 128/303.17 |
| 4,041,952 | 8/1977 | Morrison, Jr. et al. . |
| 4,411,266 | 10/1983 | Cosman ........................... 128/303.18 |
| 4,671,274 | 6/1987 | Sorochenko . |
| 4,685,459 | 8/1987 | Koch et al. ..................... 128/303.17 |
| 4,686,980 | 8/1987 | Williams et al. . |

OTHER PUBLICATIONS

"New Dimensions in Biopolar Coagulation", a brochure, F. L. Fischer.
Sugita et al, "Bipolar Coagulator . . . ", J. Neurosurg., vol. 41, Dec. 1974, pp. 777–779.

Primary Examiner—Lee S. Cohen
Attorney, Agent, or Firm—Trask, Britt & Rossa

[57] ABSTRACT

A bioplar electrosurgical forceps carries a thermocouple junction at the distal end of each of two mutually opposed prongs. The junctions are formed by welding a constantan wire directly to the ferrous metal prongs, thereby avoiding the need for electrical isolation.

4 Claims, 4 Drawing Sheets

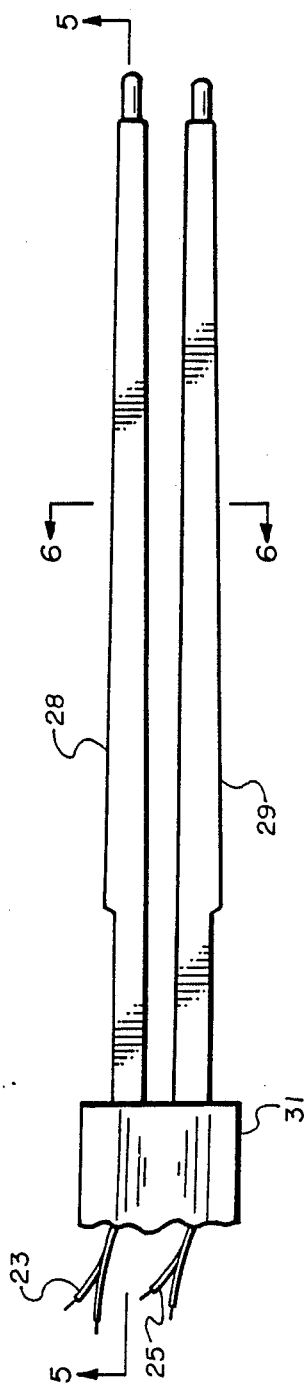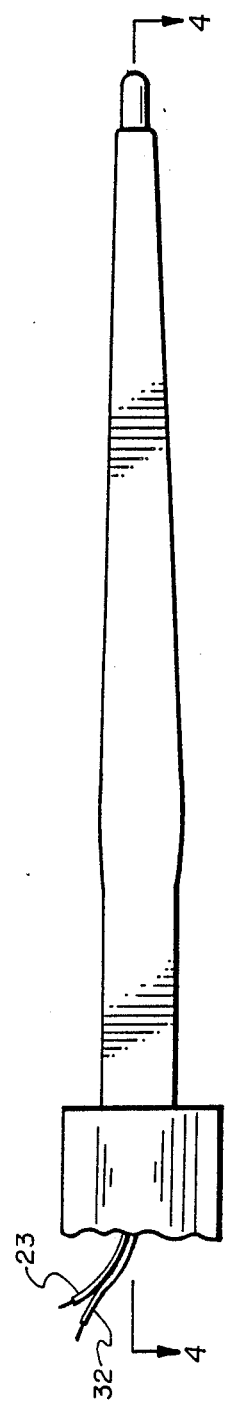

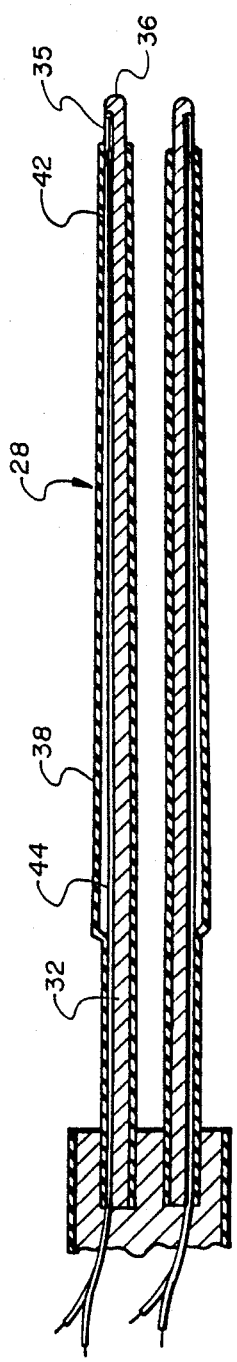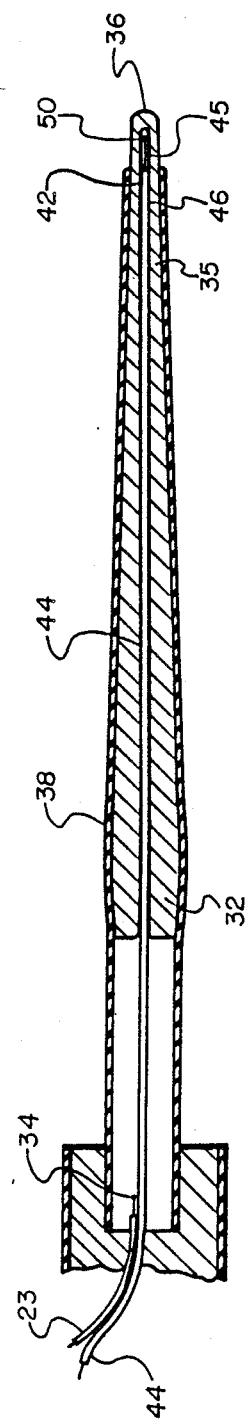
Fig. 4
Fig. 5

BIPOLAR ELECTROSURGICAL FORCEPS

BACKGROUND OF THE INVENTION

1. Field:

The present invention relates to electrosurgical apparatus of the type typically used in surgical operations for coagulating biological tissue, and provides a device for use with such electrosurgical apparatus.

2. State of the Art:

Electrosurgery is a known technique for performing cutting and coagulation procedures during surgical operations. Radio frequency (rf) current supplied by an electrosurgical generator is conveyed to a patient through the use of specialized electrodes. For example, a pair of such electrodes may be formed as opposing prongs or legs of a bipolar forceps. Reliable control of the temperature of each prong is essential. Otherwise, when the prongs are used for coagulation, tissue adhesions may result; particularly if one of the prongs is inserted further into the biological tissue than is the other prong. In such instances, the prong that is inserted to a lesser extent tends to become hotter, thereby increasing the risk of adhesions at its contact tip. If the temperature at a prong rises to above 80° C., the forceps may actually become destructive of a surgical procedure which the coagulation procedure is intended to support.

To minimize the likelihood of overheating, it has been suggested to place temperature sensors near the contacting face of the coagulating instrument. For example, U.S. Pat. No. 4,685,459 suggests embedding thermocouples as thermosensors in the machined tips of a coagulating forceps. This type of construction is relatively expensive to manufacture. Because the thermocouple is separated by insulation from the forceps, the response time of the device is reduced. Moreover, the device is inherently susceptible to the problems associated with breakdown of the electrical insulation between the thermocouple and forceps.

U.S. Pat. No. 3,685,518 discloses a surgical forceps designed to prevent the terminal parts of the forcep jaws from overheating. The disclosure of U.S. Pat. No. 3,685,518 is incorporated by reference in this disclosure for its description of bipolar high frequency surgical devices, the hazard of overheating associated with the use of such devices, and the importance of materials selection and configuration of parts in the design of such instruments.

U.S. Pat. No. 4,041,952 discloses an electrosurgical forceps with mechanical switching means carried by the tines (legs) of a forceps. Electrosurgical energy is applied to the contact surfaces (tips) of the tines by finger pressure applied to the tines to close the associated switching means.

U.S. Pat. 4,662,369 discloses a safety circuit for an electrosurgical apparatus. The circuit functions to sense rf current leakage and to respond by redirecting the output of the rf source (generator), thereby to limit leakage to below a predetermined value. The disclosure of U.S. Pat. 4,662,369 is incorporated by reference in this disclosure for its general description of electrosurgical techniques and the hazard inherent to such techniques of electrical burns.

U.S. Pats. 4,671,274; the aforesaid 4,685,459 and 4,686,908 are each directed to bipolar electrosurgical instruments of specialized design. These patents, the disclosures of which are incorporated by reference as a part of this disclosure, describe the components and uses of instruments of this type.

A number of instruments currently supplied by F. L. Fischer, Fischer MET GmbH, Schopfheimer Str, D0-7800 Freiburg, Federal Republic of Germany, are disclosed in a brochure entitled "New Dimensions in Bipolar Coagulation." The brochure describes an rf generator and associated hand pieces which purportedly eliminate burns and tissue sticking to the instrument tips. Thermosensors are integrated in the tips of the coagulation instrument to continuously measure the contact temperatures between tissue and metal. Microprocessors continuously respond to ensure that the temperature remains constant throughout the coagulation procedure.

In spite of the advances in electrosurgical techniques reported by the aforedescribed patents and commercial instruments, there remains a need in the electrosurgical art for an improved temperature sensing forceps. In particular, there remains a need for such an instrument which avoids the problems associated with electrically insulating thermocouple elements from rf-carrying prongs (legs, tines) of the forceps. The temperature-controlled (sensing) forceps available currently remain expensive and difficult to manufacture, are characterized by delayed response of the thermocouple elements by virtue of the insulating material, and are susceptible to electrical breakdown (of the insulation) between the thermocouple elements and the prongs.

SUMMARY OF THE INVENTION

The instant invention comprises a structural arrangement of components which both simplifies and improves over bipolar forceps devices of the type represented by U.S. Pat. No. 4,685,459. A significant feature of this invention is the reliance upon the material of construction of each prong of the forceps as one of the elements of a thermocouple junction at the distal end of the prong. Only one wire need thus be extended the length of the prong to the thermocouple junction. The burdensome manufacturing requirements imposed upon prior art devices by the need to physically isolate (with insulating materials) the thermocouple from the rf prongs is avoided.

The electrosurgical apparatus of this invention includes an rf generator with the general electrical characteristics of such generators utilized previously for electrosurgical applications. Such generators deliver rf energy at a bipolar output. The apparatus further includes a bipolar forceps with two individual rf-carrying prongs, electrically isolated from each other and electrically connected, e.g. through a transformer to the rf output of the generator. In effect, each prong of the forceps may be viewed as an extension of one of the bipolar elements of the rf output of the generator. The forceps includes a proximal end, adapted to be grasped by the fingers of an operator, and a distal or working end. Electrical isolation of the prongs is provided at the proximal end of the forceps by insulating material and for the remainder of the length of the forceps by physical separation. Finger pressure applied to the prongs at an intermediate location reduces the spacing at their distal ends in conventional fashion. The prongs are typically fashioned from ferrous material; e.g. surgical or stainless steel.

The distal end of each prong carries a thermocouple junction formed by joining; e.g., by spot welding a dissimilar metal (typically constantan) directly to the prong. A pair of leads connect the junction of the respective prongs to respective measuring circuits. The measuring circuits are electronically isolated, ideally in complete bipolar isolation from the rf energy circuits, specifically including the rf-carrying prongs themselves.

Both the rf generator, with its prong extensions and the measuring circuits, with their thermocouple components, may be electronically connected to appropriate computing circuitry such as that provided by a central processing unit (C('U). In particular, it is desirable to incorporate display and signal means in association with the computing circuits and the measuring circuits. In this fashion, an audible alarm or other signal can be generated in response to non-nominal conditions detected by the thermocouples. For example, it may be crucial for a surgeon to become instantly aware if the temperature at the distal end of either prong rises beyond a preselected temperature (e.g. 78° C.). Alternatively, the computing circuitry may function to attenuate the power output of the rf generator under such conditions, thereby to maintain the appropriate temperature.

DESCRIPTION OF THE DRAWINGS

In the drawings, which illustrate what is presently regarded as the best mode for carrying out the invention:

FIG. 2 is a top plan view of a hand device for use with electrosurgical apparatus made in accordance with the present invention;

FIG. 3 is a side elevational view of the device of FIG. 2;

FIG. 4 is a cross-sectional view of the device of FIG. 2, taken along the reference line 4—4 of FIG. 3;

FIG. 5 is a cross-sectional view of the device of FIG. 2 taken along the reference line 5—5;

DETAILED DESCRIPTION OF THE ILLUSTRATED EMBODIMENTS

Figure 1:
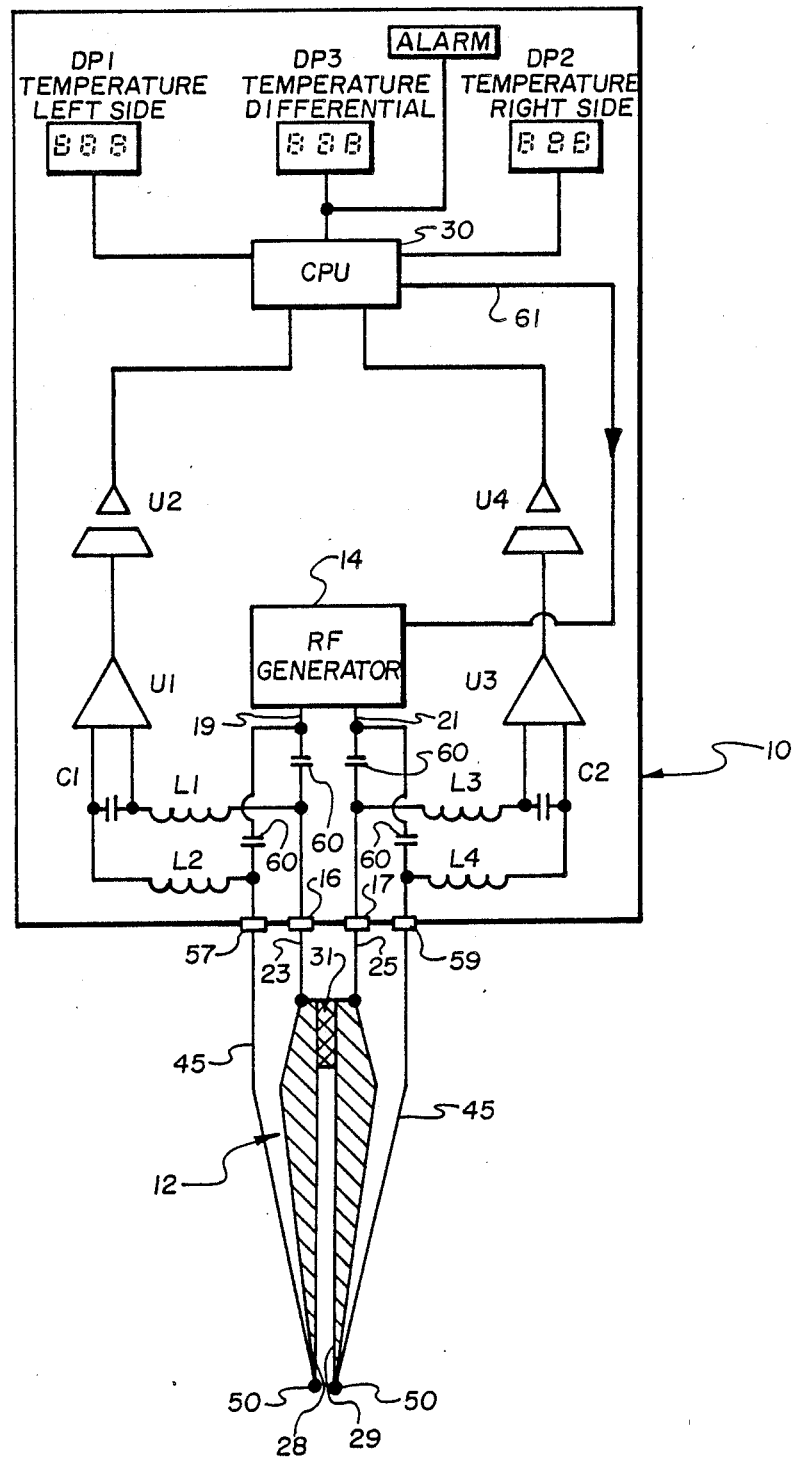
FIG. 1 is a schematic diagram of an embodiment of the invention.
Figure 6:
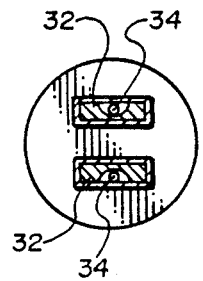
FIG. 6 is a cross-sectional view of the device of FIG. 2 taken along the reference line 6—6.

Referring to FIG. 1, there is schematically illustrated an electrosurgical apparatus 10 and a hand-held device 12 for use with apparatus 10. The apparatus 10 includes an rf generator 14 which may be selected from among the radio frequency generators presently included in commercially available electrosurgical devices. The rf generator 14 produces a radio frequency which is supplied to output connection ports 16, 17 by wires 19, 21. Hand-held device 12 is electrically connected to connection ports 16, 17 by wires 23, 25, respectively, through appropriate connectors (not shown). A conventional central processing unit (CPU) 30 is connected in circuit to the rf generator 14 in interaction with measurement and display functions, as shown. Device 12 comprises a pair of prongs 28, 29 which are electrically insulated from each other by an insulating retaining member 31.

FIGS. 2 through 6 illustrate in more detail the device 12 of the present invention. The prongs 28, 29 (FIG. 2) are firmly placed within retaining member 31. Wire 23 is electrically connected to prong 28 and wire 25 is electrically connected to prong 29. Prongs 28, 29 are identical in construction. Accordingly, only prong 28 need be discussed in detail, it being understood that the other prong 29 is similarly constructed.

Prong 28 comprises an elongated central member 32 made of a material capable of transmitting an rf frequency. The proximal end 34 of member 32 is electrically connected to wire 23, e.g. by welding as illustrated (FIG. 5). The distal end 35 of the elongated contact member 32 carries a contact surface 36 which is configurated for placement against biological tissue for application of rf frequency current. The elongated member 32 is provided with an exterior insulating coating 38, to protect the hand of an operator clasping the pair of prongs 28, 29. One suitable coating 38 comprises nylon, which may be applied by an appropriate dipping process. The elongated member 32 is provided with a longitudinal, axially extending groove 42 which accommodates an insulated wire 44. The insulated wire 44 comprises a wire core 45 surrounded by an appropriate insulation layer 46. The insulation layer 46 is stripped away so that the bare wire 45 is exposed for welding at a junction 50 to elongated member 32. The elongated member 32 and wire 45 are made of different materials selected such that the junction 50 forms a thermocouple. A suitable such junction 50 results when the wire 45 is of constantan and the elongated member 32 is of stainless steel. Wire 45 is electrically connected to apparatus 10 at inlet port 57 (FIG. 1) by an appropriate connector (not shown). The corresponding wire 45 of prong 29 is electrically connected to inlet port 59 in the same fashion.

In operation, the rf generator 14 applies an appropriate rf frequency current through wires 19, 21, 23, 25 to prongs 28, 29. The contact tips 36 of prongs 28, 29 apply the rf energy to biological tissue (not shown) to be treated. The thermocouple junctions 50 produce respective thermocouple measuring signals which are indicative of the temperatures of respective contact surfaces 36.

Means for isolating the rf frequency signal from the thermocouple signal for each prong 28, 29 in the embodiment illustrated in FIG. 1 comprises a pair of radio frequency chokes and a capacitor. Rf choke L1, rf choke L2 and capacitor C1 are associated with prong 28. One end of choke L1 is connected through input wire 19 to the elongated member 32. One end of choke L2 is connected through the wire 45 to a junction 50. The other end of chokes L1 and L2 are connected to opposite sides of the capacitor C1. The thermocouple signal of prong 29 is similarly separated from the rf frequency signal by corresponding components, rf chokes L3, L4, capacitor C2, and isolating capacitors 60.

The capacitor C1 and chokes L1 and L2 are respectively connected to a preamplifier U1 for increasing the thermocouple signal. The output of the preamplifier U1 is connected to an isolation amplifier U2 which brings the output signal from the preamplifier U1 to ground potential, producing a digitized output signal. The output of the isolation amplifier U2 is connected to the central processing unit 30. The CPU 30 is adapted to convert the thermocouple measuring signal, as delivered by amplifier U2, to a temperature measurement displayed as the left side temperature at DP1. For purposes of this disclosure, the prong 28 is regarded as the left side and the prong 29 is regarded as the right side. Other indicating means may be provided in addition to or in place of the temperature display DP1. For example, the CPU may be connected to an audio signal generator to produce a tone when a predetermined temperature is reached.

In similar fashion, chokes L3, L4 and capacitor C2 are connected through preamplifier U3, and an isolation amplifier U4, to the central processing unit 30 where the thermocouple signal from the thermocouple junction 50 on the right side (prong 29) is translated to a temperature measurement. This temperature measurement is displayed as the right side temperature at DP2, as illustrated. Various other display means may be used either in addition to or in place of the visual display DP2 as in the case of display DP1.

As illustrated, a third visual display DP3 is provided for displaying the difference in temperature between the contact surface 36 of prong 28 and the contact surface 36 of prong! 29. There is also illustrated an audible alarm, controlled by CPU 30 to signal any temperature differential regarded as undesirable.

The CPU can be programmed to adjust the output of the rf generator at leads 19, 21 as desired. In the particular embodiment illustrated, a control feedback signal is generated by the central processing unit 30 to the rf generator 14 as indicated by line 61. In the preferred operation of the present invention, the central processing unit 30 is programmed such that when the temperature of the contact surface 36 of either prong 28 or 29 rises above a predetermined temperature, the rf generator output will be adjusted appropriately so as to reduce the temperature at the contact surface 36. This adjustment is typically effected by lowering the energy supplied to wires 19, 21. For example, a central processing unit 30 may be programmed such that a temperature in excess of 80° C. at contact surface 36 induces a feedback signal to occur, thereby adjusting the rf generator output. CPU 30 may be programmed such that when a predetermined differential between the respective contact surfaces 36 of prongs 28, 29 is obtained, the rf generator output either will be reduced until the temperature differential is brought to within the desired limits, and/or it will shut off.

The device 12 is of simple construction and very durable. Because the elongated member 32 comprises one of the junctions of the thermocouple, it is not necessary to insulate the thermocouple as in previous devices of this type. The absence of insulation between the thermocouple junction 50 and the member 32 results in faster temperature response and avoids the hazard of breakdown of the insulation between the thermocouple and the prongs.

Figure 7:
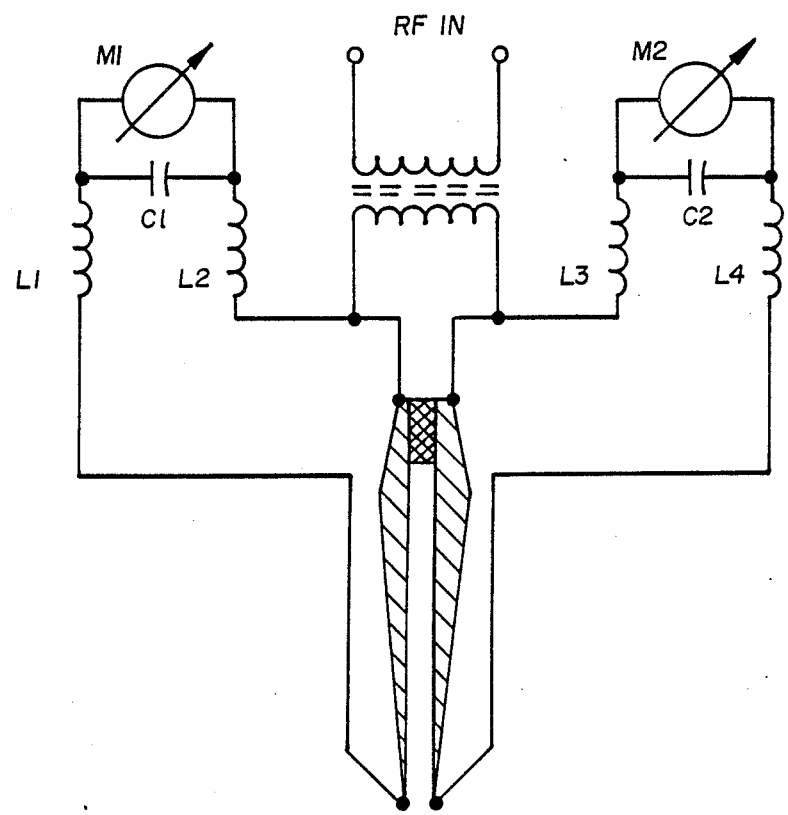
FIG. 7 is a schematic diagram of an alternative embodiment of the invention.

FIG. 7 is a generalized representation of the present invention, one embodiment of which is that illustrated by FIG. 1. Measuring circuit M1 and M2 are provided for converting the signals from junctions 50 of prongs 28, 29 to temperature measurements. M1 and M2 may comprise amplifier driven optocoupler circuits, for example.

In the preferred embodiment, the circuitry for isolating the thermocouple measuring signal from the rf frequency is illustrated as part of the electrosurgical apparatus 10. In practice, it may be more convenient for the isolating circuitry to be included in the hand-held device 12.

Reference herein to details of the illustrated embodiments is not intended to limit the scope of the claims which themselves recite those features regarded as important to the invention.

What is claimed:

1. An electrosurgical apparatus comprising:
   an rf generator with first and second output terminals;
   a hand-held forceps formed of first and second prongs, respectively, said prongs being electrically coupled to respective said terminals;
   each of said prongs having a proximal end and a distal end formed of a first metal, said prongs being positioned in approximately parallel spaced alignment with their proximal ends held in fixed non-conductive relationship and their distal ends spaced from each other in opposed working relationship;
   the distal ends of said prongs respectively comprising surgical contact surfaces electrically connected to said generator, and carrying a thermocouple junction between said first metal and a second metal in a groove separated from said contact surfaces;
   conductors extending from respective said thermocouple junctions in mechanical association with but in non-conductive relationship with respective said prongs; and
   measurement circuit means electronically associated with said conductors to detect signals from respective said junctions and to convert said signals into respective temperature measurements, said measurement circuit means being electronically isolated from said rf generator.

2. Apparatus according to claim 1 wherein each of said prongs is conductive between its proximal and distal ends and said conductors are formed of said second metal.

3. Apparatus according to claim 2 wherein said proximal ends are held by an insulating fixture.

4. Apparatus according to claim 3 wherein said prongs are made of ferrous metal and said conductors are made from constantan metal.

* * * * *

UNITED STATES PATENT OFFICE
CERTIFICATE OF CORRECTION

Patent No. 4,938,761             Dated  JULY 3, 1990

Inventor(s) FRIEDER H. ENSSLIN

It is certified that error appears in the above-identified patent and that said Letters Patent is hereby corrected as shown below:

On the first page, before the drawings, in the left column after [22] Filed:, delete "Mar. 6, 1990" and insert --Mar. 6, 1989--.

Signed and Sealed this

Eleventh Day of June, 1991

Attest:

HARRY F. MANBECK, JR.

*Attesting Officer*   *Commissioner of Patents and Trademarks*